(12) United States Patent
Wienand et al.

(10) Patent No.: US 7,893,510 B2
(45) Date of Patent: Feb. 22, 2011

(54) HIGH TEMPERATURE-STABLE SENSOR

(75) Inventors: Karlheinz Wienand, Aschaffenburg (DE); Karlheinz Ullrich, Gross-Umstadt (DE)

(73) Assignee: Heraeus Sensor Technology GmbH, Hanau (DE)

( * ) Notice: Subject to any disclaimer, the term of this patent is extended or adjusted under 35 U.S.C. 154(b) by 0 days.

(21) Appl. No.: 11/179,109

(22) Filed: Jul. 12, 2005

(65) Prior Publication Data

US 2006/0170015 A1 Aug. 3, 2006

(30) Foreign Application Priority Data

Jul. 14, 2004 (DE) ................. 10 2004 034 192

(51) Int. Cl.
*H01L 21/76* (2006.01)
(52) U.S. Cl. .................................... 257/414
(58) Field of Classification Search ......... 257/252–253, 257/467, 414
See application file for complete search history.

(56) References Cited

U.S. PATENT DOCUMENTS

| | | | | |
|---|---|---|---|---|
| 4,294,679 | A | * | 10/1981 | Maurer et al. ............... 204/426 |
| 5,958,340 | A | * | 9/1999 | Meyer et al. ................. 422/90 |
| 6,109,094 | A | * | 8/2000 | Baranzahi et al. .......... 73/31.06 |
| 2002/0036138 | A1 | * | 3/2002 | Kuroki et al. ............... 204/426 |
| 2002/0108870 | A1 | * | 8/2002 | Thoreson .................... 205/781 |
| 2002/0108871 | A1 | * | 8/2002 | Wang et al. ................. 205/784 |
| 2002/0117397 | A1 | * | 8/2002 | Anderson et al. ........... 204/424 |
| 2002/0139670 | A1 | * | 10/2002 | Beckmeyer et al. ......... 204/429 |
| 2003/0209433 | A1 | * | 11/2003 | LaBarge et al. ............. 204/426 |
| 2004/0016228 | A1 | | 1/2004 | Yasui et al. |

FOREIGN PATENT DOCUMENTS

| | | |
|---|---|---|
| DE | 35 04 498 A1 | 8/1986 |
| DE | 10 2004 015 467.8 | 3/2004 |
| EP | 0 738 385 B1 | 7/2002 |
| JP | 2003-215092 A | 7/2003 |
| JP | 2003-328848 A | 11/2003 |

OTHER PUBLICATIONS

U.S. Appl. No. 11/090,423, filed Mar. 2005, Weiland, et al.
German translation of JP Examination Report issued Sep. 24, 2010 in counterpart JP Application No. JP 2005-204890. (Partial English Translation attached).

* cited by examiner

*Primary Examiner*—Wael M Fahmy
*Assistant Examiner*—Sarah K Salerno
(74) *Attorney, Agent, or Firm*—Panitch Schwarze Belisario & Nadel LLP

(57) ABSTRACT

A high temperature-stable sensor is provided in which electrodes on a substrate or an insulation layer are in contact with a sensitive layer, wherein the electrodes have platinum, rhodium, or iridium or an electrically conductive oxide layer. For this purpose, an intermediate product is provided as a platform chip, which has a deposited layer made of platinum, rhodium, or iridium or an alloy of platinum, rhodium, or iridium and is covered by an electrically conductive oxide. From the deposited layer, a conductive structure is formed and thus a platform chip is created with an electrically conductive structure subject to external influences. This structure has an electrically conductive oxide and/or its parts have long-term, stable characteristic resistance curves under high-temperature loading above about 500° C., especially between about 600° C. and 950° C. A sensor with a gas-sensitive layer formed as a gas-sensitive sensor is preferred.

14 Claims, 2 Drawing Sheets

HIGH TEMPERATURE-STABLE SENSOR

BACKGROUND OF THE INVENTION

The present invention relates to a platform chip or high temperature-stable sensor, in which electrodes arranged on a substrate are in contact with a sensitive layer. The invention also relates to an intermediate product, production methods, and applications, particularly to methods for combustion control and for exhaust-gas recirculation.

From German published patent application DE 35 04 498 A1, a high-temperature gas sensor is known for determining gas components in automobile exhaust gases, in which thin-film semiconductor sensors and a heating arrangement are arranged on a substrate. The heating arrangement has a meander shape and the semiconductor sensors engage each other like combs.

European Patent EP 0 738 385 B1 describes a lambda probe having sufficient mechanical and thermal stability relative to the hot and pulsing exhaust gas from internal-combustion engines. For this purpose, a contact track made of platinum is applied on $Al_2O_3$ via a bonding agent.

Material fluxes are determined with heated sensors by the energy consumption of the sensor. High-temperature sensors contain platinum-coated chips and are used, for example, at temperatures up to about 450° C. for CO measurement in exhaust gases. At higher temperatures, the chips wear out and therefore are not suitable for long-term use in the range above 600° C., especially above 700° C.

In particular, the resistance or the conductivity of the electrodes changes, whereby the measurements become imprecise and unusable.

BRIEF SUMMARY OF THE INVENTION

An object of the present invention is to provide sensors for determining gas concentrations, which require platform-chip heating in order to determine or to measure particular gas fractions, such as $O_2$, in a range of about 650° C. to 950° C., or which can be used to perform long-term measurements in hot exhaust gases above about 600° C.

This problem is solved with platform chips or sensors, whose electrodes standing in contact with the gas-sensitive layer have iridium, rhodium, a platinum alloy, a rhodium alloy, an iridium alloy, or an electrically conductive oxide layer. These sensors are platform chips on which a sensitive layer is carried.

For this purpose, platform chips are provided, which exhibit particularly low changes in their characteristic resistance curves at temperatures of about 500° C. to 1100° C. within a year. In particular, with applications up to about 1000° C., the characteristic resistance curve remains so stable that the functionality of the sensors is maintained over several years and is stable up to about 950° C. over several decades. The characteristic resistance curve characterizes the electrical resistance of the electrical conductor over a certain temperature range. The characteristic resistance curve must be constant in all parts of the conductive structure.

The platform chips forming the basis of the present invention are electrical components, which have at least one substrate, one electrically functional pattern, and at least one other layer. The electrical pattern is preferably formed as an electrically conductive structure or a layer, which has, in addition to platinum, rhodium or iridium, an electrically conductive oxide. The other layer is preferably a sensitive layer or a heater.

This electrical pattern distinguishes itself by its resistance to external influences at temperatures of about 500° C. to 1100° C., in particular by a stable characteristic resistance curve. Other optional conductive structures, layers, or coatings need not have this resistance, because they are used in special configurations, for example with other unprotected conductive structures of a multiple sensitivity sensor or an optional unprotected heater or temperature sensor.

Suitable platform chips have a coating made of an electrically conductive oxide or a coating made of iridium, rhodium, or platinum, which is covered by an electrically conductive oxide.

Other suitable platform chips have, in addition to an outer coating made of an iridium alloy, a rhodium alloy, or a platinum alloy, and also inner electrically insulated conductive layers, which can be formed as a heater and/or a temperature sensor.

A preferred iridium alloy contains platinum (Pt), rhenium (Re), or rhodium (Rh) or a mixture of Pt, Re, and Rh. A preferred platinum alloy contains at least about 5 wt. % Rh and/or Ir. Iridium oxide and rhodium oxide are the preferred electrically conductive oxides.

An intermediate product according to the invention is a platform chip with a layer made of platinum, rhodium, or iridium or an alloy made of platinum, rhodium, or iridium, on which an electrically conductive oxide is formed or applied. A conductive structure is structured from the layer by photolithography.

By depositing a sensitive dielectric on the outer coating of this platform chip, a specific, sensitive, high temperature-stable sensor is obtained. The sensitive layer has the property that it detects external influences. It is open to external influences, whereby it also does not protect the electrodes from external influences.

In a simple embodiment, the platform chip can be formed as a sensitive sensor, if it has a sensitive layer. The sensitive layer is formed as a dielectric and has a sensing effect, such that under external influences, its dielectric properties are adjustable.

In one preferred embodiment, the sensitive layer is formed as a gas-sensitive layer. Gas-sensitive layers have the property of being permeable to gases, and their electrochemical behavior is thereby changed. Therefore, however, the electrodes located beneath the gas-sensitive layer are still subjected to the influences of the atmosphere.

Thus, high temperature-stable gas sensors are provided, in which a gas-sensitive dielectric is arranged on outer electrodes.

With this arrangement, pollutants from burner exhaust gases can be tested, which requires heating of the chip from about 650° C. to 950° C. depending on the type of gas. Furthermore, gas pollutants in hot exhaust gases above about 600° C., like those output, for example, from internal-combustion engines, can be continuously tested for pollutants.

The invention now enables the operation to be optimized in terms of lower environmental loading and in terms of efficiency from set parameters of the burner or the vehicle internal-combustion engine.

Thus, a combustion mixture for the burner or internal-combustion engine can be constantly optimized. In particular, a method for partial exhaust-gas recirculation into an air-inlet region of a vehicle internal combustion engine is provided, in which a mixture of exhaust gas and incoming air, which can be adjusted by regulation, is fed to the engine. At least one exhaust-gas component is determined by a high-temperature gas sensor, and an amount of fuel is fed depending on the determined concentration in the exhaust gas, and the measured exhaust gas is measured at over about 500° C.

Furthermore, the comb-like electrodes are preferably arranged opposing each other.

In another preferred embodiment, the electrodes have a platinum-rhodium alloy, which forms, in particular, a rhodium-oxide skin. The rhodium-oxide skin is electrically conductive and protects the platinum-rhodium alloy from further oxidation or sublimation. Preferred platinum-rhodium alloys contain about 5 to 50 wt. % rhodium, especially about 10 to 20%.

In another preferred embodiment, a high-temperature chip comprises, in addition to the sensor unit, at least one other electrical circuit, especially a heating structure. Particularly advantageously, the temperature of the heating unit is controlled by another circuit formed as a temperature sensor. The heating device and the temperature sensor can be protected by passivation layers, so that their resistance behavior at high temperatures does not degrade. Therefore, the electrical circuits can be embodied in a known way for forming a heating unit and/or a temperature sensor, e.g., as meander-shaped heating electrodes made of platinum.

A high-temperature sensor according to the following invention withstands temperatures over about 600° C., especially temperatures of about 650° C. to 1100° C., and even about 800° C. to 950° C. under long-term loading over several decades.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
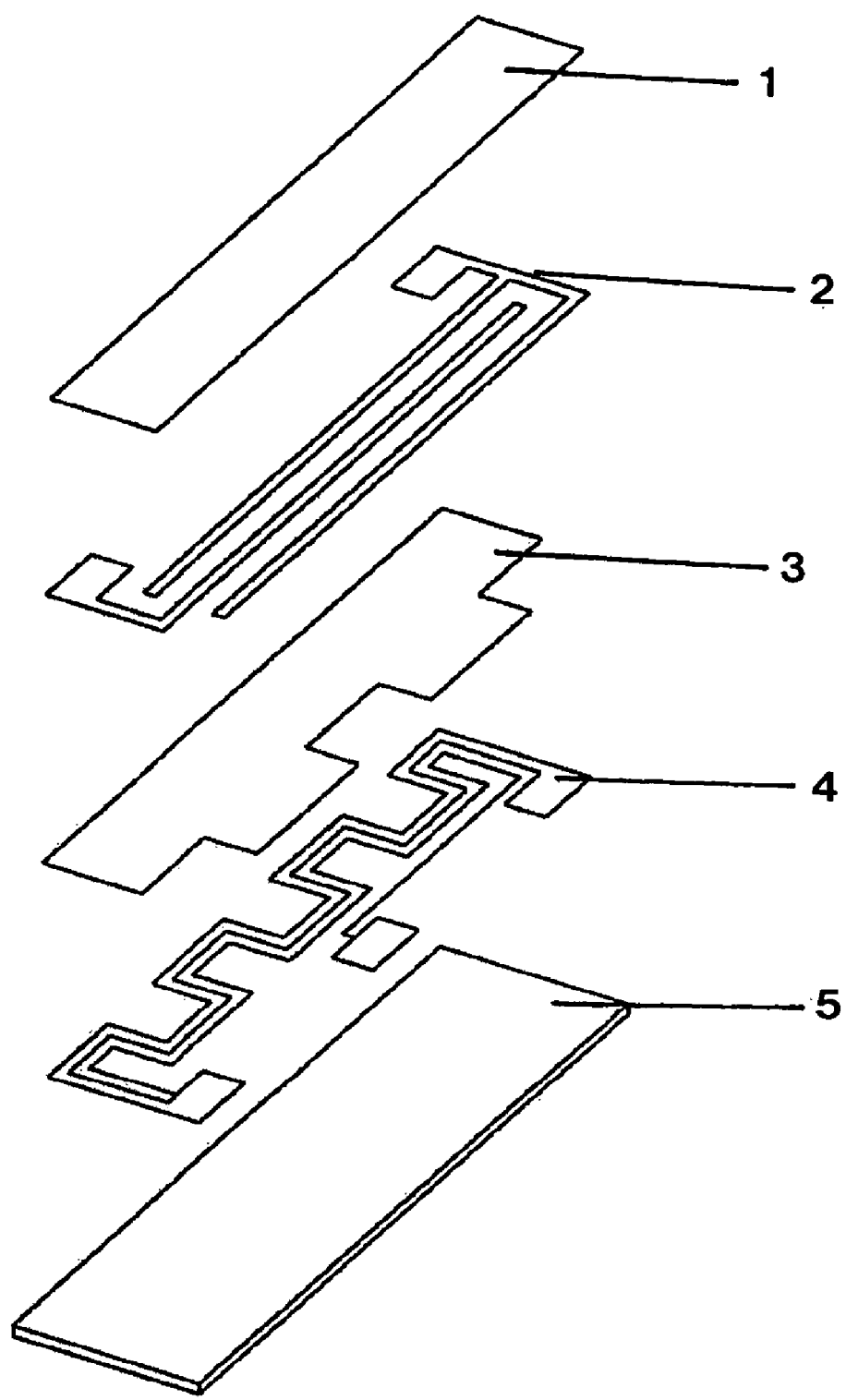
FIG. 1 is an exploded perspective view of a platform chip according to an embodiment of the invention.

In FIG. 1, the shown sensor has an active sensor layer 1 on an IDK structure 2 (IDK=inter-digital capacitor) made of a platinum alloy or an iridium alloy and an oxide substrate 5 made particularly of aluminum oxide. An optional iridium or platinum structure 4 with insulation layer 3 lying above this structure lies between the sensor layer 1 on the IDK structure 2 and the oxide substrate 5. These optional conductive structures can be formed as a heater and/or temperature sensor.

Figure 2:
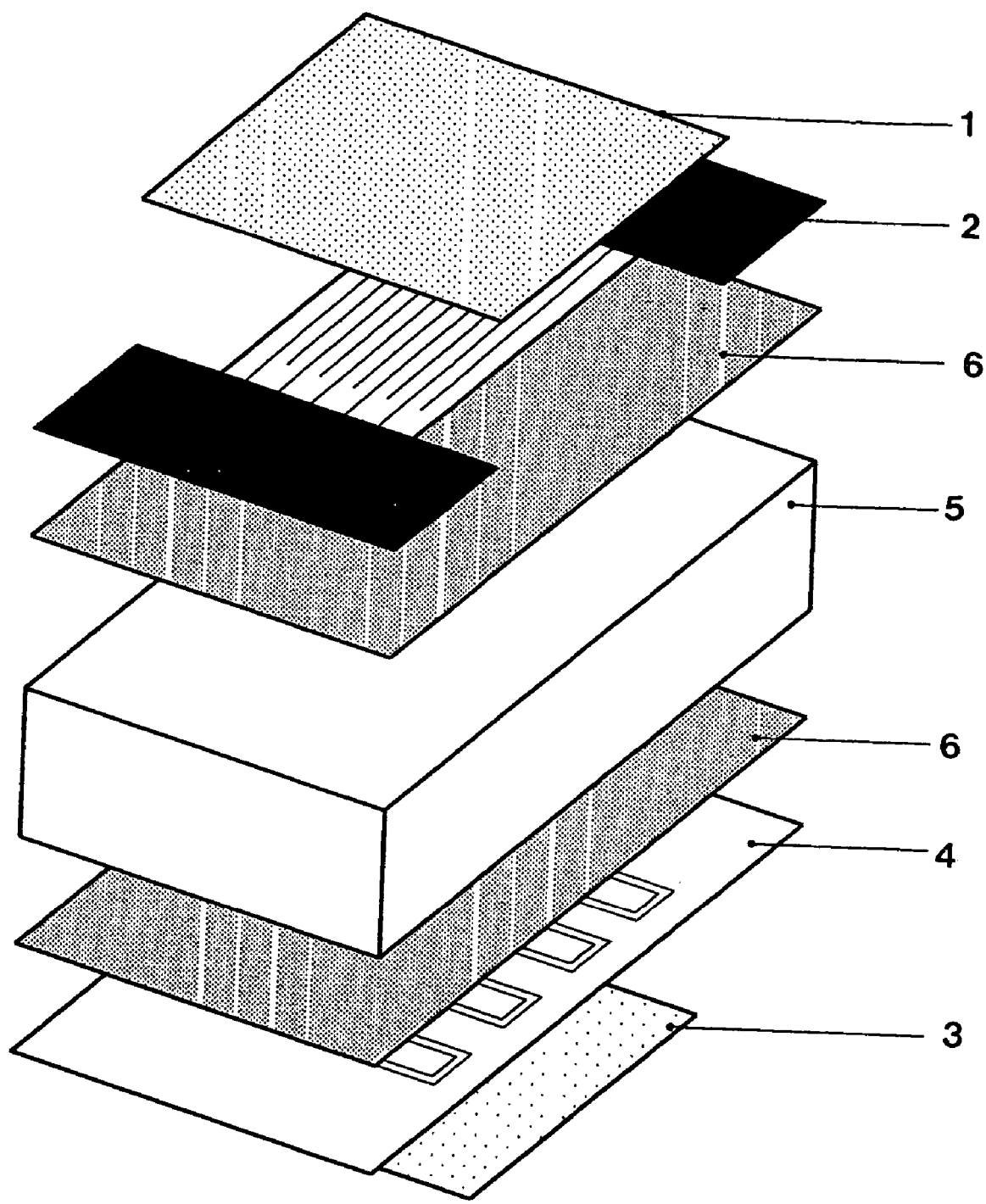
FIG. 2 is an exploded perspective view of a substrate coated on two sides as a platform chip according to another embodiment of the invention.

FIG. 2 shows the substrate 5 as a platform chip coated on both sides with an optional adhesive layer 6. A heater 4, which is covered by a protective layer 3, is adhered to one side. Electrically conductive tracks are adhered to the other side on the adhesive layer 6 and are covered by a gas-sensitive layer 1.

With the heater 4, the sensitive layer 1 is heated to its ideal measurement temperature. In addition, a temperature sensor can be used for temperature control and regulation of the heater. The temperature sensor can be formed in a layer 4 with the heater or can be arranged, covered with an insulation layer 3, between the substrate 5 and the conductive track 2.

For manufacturing sensitive sensors, platform chips can be provided, in which a substrate 5 is coated with a temperature sensor 4, an insulation layer 3, a heater 4, another insulation layer 3, and an IDK structure 2, before this intermediate platform chip is coated in a last processing step with a specific, sensitive dielectric 1 and thereby obtains its special function as a sensitive sensor. The final deposition of a gas-sensitive layer 1 thus creates a gas sensor. However, any other sensitive layer 1 can also be deposited on the platform chip base, which then imparts to the sensor its specific sensing properties. Platinum-rhodium 10 and platinum-rhodium 20 are suitable commercially available alloys for the IDK structure.

For manufacturing a sensor, an electrically conductive layer 2 is deposited on a substrate 5. Optionally, the substrate is coated with a diffusion barrier and opionally also with an adhesive layer 6, so that the metal can be affixed to the base. Preferably, the coating is performed by vapor deposition or sputtering technology, and then etching of a pattern. A coating or the formation of an adhesive layer 6 according to the still unpublished German patent application DE 10 2004 015 467.8 is similarly suitable. Furthermore, for gas-sensitive sensors, a gas-sensitive layer 1 is deposited on the outer metallic layer 2. Embodiments with an additional heater 4 and a protective layer 3 can expand the range of applications.

Additional inner metal layers 4 essentially comprise conductive arrangements 4 arranged between two electrically insulating layers 3 or 5. A portion of the inner metal layers 4, often designated as contact pads, projects above the layers 3 and is connected to the electric power source.

The structure of the metal layers 2 or 4 can be formed with a meander shape or as a capacitor of interdigitated comb structures. Also, the inner metal structure layers 4 can consist completely of an iridium or platinum alloy. However, the uncovered conductive tracks 2 merely need to be formed with a thickness below about 5 μm, preferably below about 2 μm, as the platinum alloy or iridium alloy, in order to make the chip suitable for long-term use at high temperatures above about 500° C., particularly above about 700° C.

Preferred platinum alloys contain about 0.05 to 50 wt. % rhodium, preferably about 5 to 20 wt. % rhodium. An iridium alloy preferably contains rhenium and/or rhodium. The chip is suitable for determining exhaust gas components in a temperature range of about 500° C. to 1000° C.

Production of a Platform Chip

Example 1

A substrate 5 made of aluminum oxide is coated with an iridium or platinum suspension according to the still unpublished German patent application DE 10 2004 015 467.8 by multiple applications of the suspension and subsequent drying to form a layer thickness of 0.7 μm. On this layer, a one-time application of a rhodium suspension is performed. After its drying and firing (burning in), a pattern 2 is generated from the metal layer 2. This can be generated by known etching methods according to photolithographic methods or by scribing by a laser. In this manner, conductive tracks 2 are generated, which can be shaped in the form of interdigitated combs 2. The characteristic resistance curve remains constant in series production.

Example 2

A substrate 5 made of aluminum oxide is coated with an iridium or platinum suspension according to the still unpublished German patent application DE 10 2004 015 467.8 by multiple applications of the suspension and subsequent drying to form a layer thickness of 1 μm. According to the method of Example 1, a pattern 4 is generated in the metal layer. In this manner, conductive tracks are generated, which can be shaped in the form of a meander 4 or interdigitated combs 2.

These conductive tracks are coated with an electrically insulating material 3. In turn, conductive tracks are generated on this insulation layer 3 as before on the substrate 5. Another insulating layer 3 is formed, followed by a new application of a conductive track. On the outermost conductive track, a one-time application of a rhodium suspension is performed followed by the same steps as in Example 1.

Example 3

A substrate 5 made of aluminum oxide is coated over the entire surface with platinum by the PVD method of electron-beam vaporization. This coating 4 is structured into a heating meander 4 by etching technology according to lithography. On this layer, a seal 3 is realized by high temperature-resistant layers made of metal oxides and glass ceramic. On the other side of the substrate 5, an insulation layer 6, preferably made of metal oxides, is applied over the entire surface. On this layer, a platinum-rhodium alloy is applied by electron-beam vaporization, which is structured by photolithographic and etching methods into comb-like electrodes 2. On this layer, a high-temperature treatment is performed for forming an outer oxide layer.

Example 4

This Example is analogous to Example 3, with the difference that for improved bonding strength on the metal oxide layer 6 or on the ceramic 5, a noble-metal suspension according to German patent application DE 10 2004 015 467.8 is applied and fired.

The platform chips produced according to Examples 1 to 4 exhibit little change in their characteristic resistance curves for long-term use in the high-temperature range of about 500° C. to 1000° C. and enable high functionality lasting over years for high-temperature applications, especially between about 600° C. and 900° C.

Production of a Sensitive Sensor

Example 5

The outer pattern 2 of the platform chips produced according to Examples 1 to 4 is coated with a specific sensitive material 1, e.g., based on gallium oxide. For the coating 1 with a gas-sensitive material 1, a gas sensor is produced with long-lasting functionality of the platform chip forming its basis.

The sensors are suitable for measuring exhaust-gas flows and can be used especially for controlling the exhaust-gas recirculation of internal combustion engines. Therefore, they can contribute, on one hand, to better utilization of the energy of the fuel and, on the other hand, to reduce the pollutants in the exhaust gas. The selection of the substrate material depends on whether the sensor is operated at 650° C., 750° C., 850° C., or above. Preferably, the chips are formed as platform chips. These distinguish themselves in that the top and/or rear sides of a substrate made of ceramic, aluminum oxide, glass, sapphire, crystalline quartz, or electrically insulated metal are coated with a heater and/or a temperature sensor.

In addition to the common coating methods, the coating method of the still unpublished German patent application DE 10 2004 015 467.8 is also suitable.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A platform chip for depositing a sensitive layer thereon, wherein the platform chip comprises a substrate, an electrically insulating material, and a first electrically conductive structure, wherein the first electrically conductive structure is subject to external influences and does not function as a sensitive layer, the first electrically conductive structure comprises a deposited layer and a coating in direct contact with the deposited layer, the deposited layer comprises a material selected from at least one of platinum, rhodium, iridium, and alloys thereof and the coating comprises an electrically conductive oxide selected from the group consisting of iridium oxide and rhodium oxide, and wherein the first electrically conductive structure has long-term stable characteristic resistance curves under high-temperature loading over about 500° C. and is in direct contact with the electrically insulating material and is configured for direct contact with a sensitive layer.

2. The platform chip according to claim 1, wherein the first electrically conductive structure has long-term stable characteristic resistance curves under high-temperature loading between about 600° C. and 950° C.

3. The platform chip according to claim 1, wherein the platform chip further comprises a second electrically conductive structure covered with the electrically insulating material and arranged on and in direct contact with the substrate, and wherein the first electrically conductive structure comprises a material selected from at least one of iridium, rhodium, a platinum alloy, a rhodium alloy, and an iridium alloy and is arranged on and in direct contact with at least one of the electrically insulating material and the substrate.

4. The platform chip according to claim 1, wherein the first electrically conductive structure is arranged on the electrically insulating material, and wherein a second electrically conductive structure selected from at least one of iridium, rhodium, a platinum alloy, a rhodium alloy, and an iridium alloy is deposited onto a different side of the substrate from the first electrically conductive structure.

5. The platform chip according to claim 1, having a form of a high temperature-stable sensor.

6. The platform chip according to claim 1, wherein the first electrically conductive structure is arranged on the substrate, and wherein the substrate comprises $Al_2O_3$.

7. A sensor chip comprising a substrate, a sensitive layer, an electrically insulating material, and a first electrically conductive structure, wherein the first electrically conductive structure is subject to external influences and does not function as a sensitive layer, the first electrically conductive structure comprises a deposited layer and a coating in direct contact with the deposited layer, the deposited layer comprises a material selected from at least one of platinum, rhodium, iridium, and alloys thereof and the coating comprises an electrically conductive oxide selected from the group consisting of iridium oxide and rhodium oxide, and wherein the first electrically conductive structure has long-term stable characteristic resistance curves under high-temperature loading over about 500° C. and is in direct contact with the electrically insulating material and with the sensitive layer.

8. The sensor chip according to claim 7, wherein the first electrically conductive structure has long-term stable characteristic resistance curves under high-temperature loading between about 600° C. and 950° C.

9. The sensor chip according to claim 7, wherein the first electrically conductive structure is arranged on the substrate, the first electrically conductive structure comprises electrodes, and the sensitive layer is in direct contact with the electrodes and with the electrically insulating material.

10. The sensor chip according to claim 9, having a form of a high temperature-stable sensor.

11. The sensor chip according to claim 9, wherein the chip has several conductive structures.

12. The sensor chip according to claim 9, wherein the chip comprises a gas-sensitive unit.

13. The sensor chip according to claim 12, having a form of a high temperature-stable sensor.

14. The sensor chip according to claim 7, wherein the first electrically conductive structure is arranged on the substrate, and wherein the substrate comprises $Al_2O_3$.

* * * * *